(12) United States Patent
Nishijima

(10) Patent No.: US 12,702,374 B2
(45) Date of Patent: Aug. 11, 2026

(54) X-RAY DETECTOR AND CONTROL METHOD

(71) Applicant: Canon Kabushiki Kaisha, Tokyo (JP)

(72) Inventor: Akira Nishijima, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 153 days.

(21) Appl. No.: 18/596,188

(22) Filed: Mar. 5, 2024

(65) Prior Publication Data

US 2024/0298994 A1 Sep. 12, 2024

(30) Foreign Application Priority Data

Mar. 6, 2023 (JP) ................................ 2023-033784

(51) Int. Cl.

| | |
|---|---|
| ***G01T 1/24*** | (2006.01) |
| ***A61B 6/00*** | (2006.01) |
| ***A61B 6/42*** | (2024.01) |
| *A61B 6/03* | (2006.01) |

(52) U.S. Cl.

CPC ............ *A61B 6/542* (2013.01); *A61B 6/4241* (2013.01); *G01T 1/24* (2013.01); *A61B 6/032* (2013.01)

(58) Field of Classification Search

CPC ....... A61B 6/542; A61B 6/4241; A61B 6/032; G01T 1/24

See application file for complete search history.

(56) References Cited

U.S. PATENT DOCUMENTS

| | | | | |
|---|---|---|---|---|
| 5,729,584 A * | 3/1998 | Moorman | .......... G01T 1/20182 378/146 |
| 11,369,330 B2 | 6/2022 | Kaneko et al. | |
| 2018/0333124 A1 | 11/2018 | Kaneko et al. | |

FOREIGN PATENT DOCUMENTS

| | | | |
|---|---|---|---|
| CN | 113274044 A * | 2/2020 | .............. A61B 6/03 |
| JP | 2010-230408 A | 10/2010 | |
| JP | 2011-87781 A | 5/2011 | |
| JP | 2018-192237 A | 12/2018 | |
| JP | 7337642 B2 * | 10/2019 | .............. A61B 6/03 |

* cited by examiner

*Primary Examiner* — Uzma Alam
*Assistant Examiner* — Fani Polyzos Boosalis
(74) *Attorney, Agent, or Firm* — Oblon, McClelland, Maier & Neustadt, L.L.P.

(57) ABSTRACT

An X-ray detector according to an embodiment is an X-ray detector of photon counting type including a plurality of detection elements and a voltage supply device configured to supply the detection elements with a voltage for reading out electric charges accumulated in the detection elements irradiated with X-rays, and the X-ray detector includes processing circuitry configured to: identify target elements from among the detection elements based on information that is acquired during a CT scan using the X-ray detector, each of the target elements causing a large current to flow through a circuit between the target element and the voltage supply device; and stop voltage supply from the voltage supply device to at least some of the target elements.

6 Claims, 7 Drawing Sheets

FIG.1A

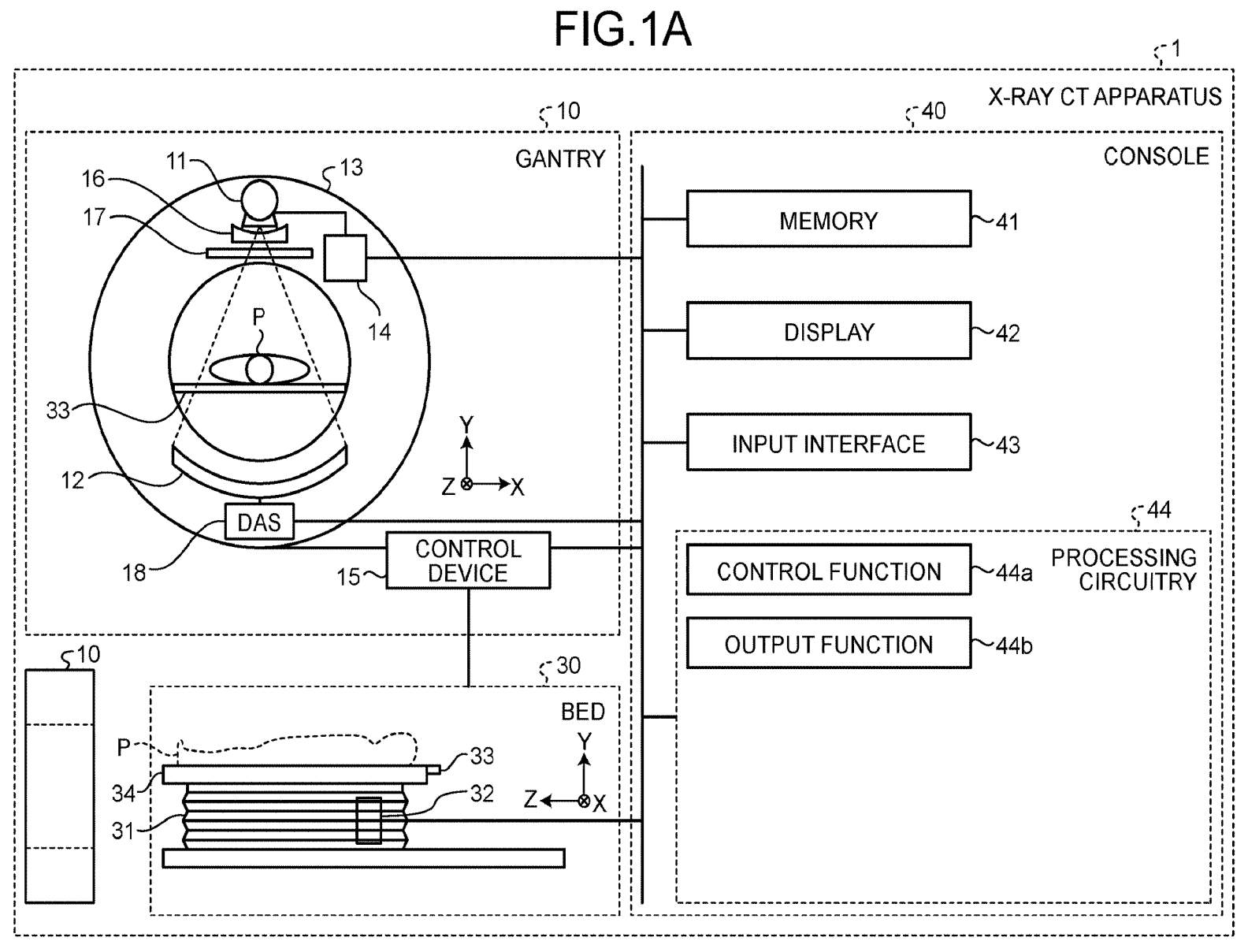

X-RAY CT APPARATUS
1
CONSOLE
40
MEMORY
41
DISPLAY
42
INPUT INTERFACE
43
PROCESSING CIRCUITRY
44
CONTROL FUNCTION
44a
OUTPUT FUNCTION
44b
GANTRY
10
CONTROL DEVICE
15
DAS
18
BED
30
Y
X
Z
P
11
12
13
14
16
17
33
31
32
34

X-RAY DETECTOR AND CONTROL METHOD

CROSS-REFERENCE TO RELATED APPLICATIONS

This application is based upon and claims the benefit of priority from Japanese Patent Application No. 2023-033784, filed on Mar. 6, 2023; the entire contents of which are incorporated herein by reference.

FIELD

Embodiments described herein relate generally to an X-ray detector and a control method.

BACKGROUND

There is known an X-ray CT apparatus using a photon counting type X-ray detector. In a CT scan using the photon counting type X-ray detector, incident X-ray photons are counted for every optional number of energy bands (bins). Due to this, an X-ray CT image can be reconstructed, and substance discrimination processing can be performed for every optional number of substances. Furthermore, circuit noise can be theoretically suppressed, so that image quality can be maintained even in a case of performing a CT scan with a low dose.

The photon counting type X-ray detector is implemented by a semiconductor detector, for example. Specifically, X-ray detection signals can be acquired by applying a voltage to electric charges generated in the semiconductor detector due to incidence of X-rays to be output.

BRIEF DESCRIPTION OF THE DRAWINGS

FIG. 1A is a block diagram illustrating an example of a configuration of an X-ray CT apparatus according to an embodiment;

FIG. 4 is a diagram illustrating an example of information that is acquired during a CT scan according to the first embodiment;

FIG. 5 is a diagram for explaining control of voltage supply to a target element according to the first embodiment;

DETAILED DESCRIPTION

Figure 1B:
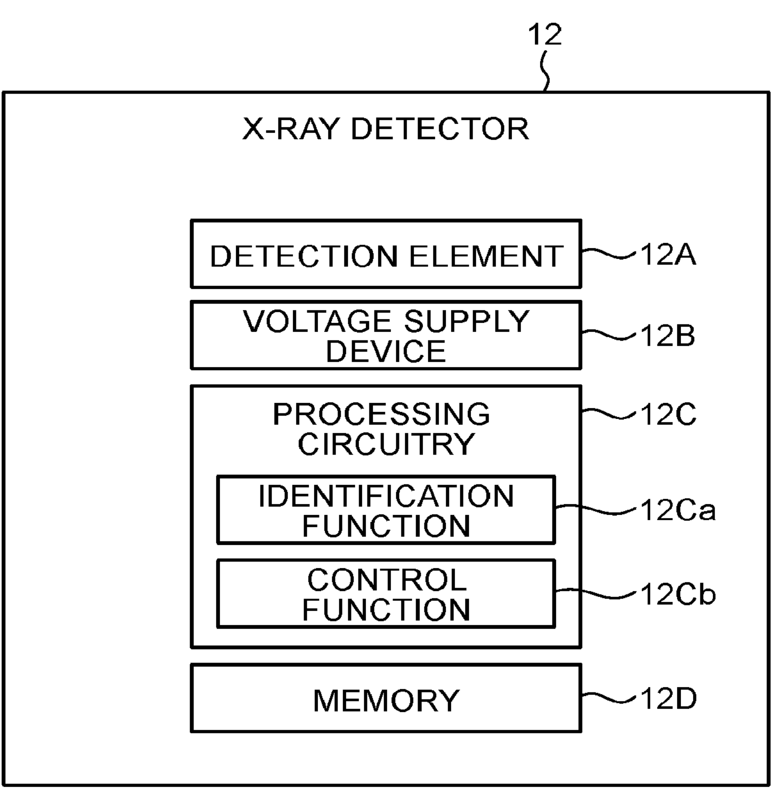
FIG. 1B is a block diagram illustrating an example of a configuration of an X-ray detector according to a first embodiment.

The following describes embodiments of an X-ray detector and a control method in detail with reference to the attached drawings.

A first embodiment exemplifies an X-ray CT apparatus 1 including a photon counting type X-ray detector 12. FIG. 1A is a block diagram illustrating an example of a configuration of the X-ray CT apparatus 1 according to the first embodiment. For example, the X-ray CT apparatus 1 includes a gantry 10, a bed 30, and a console 40.

In FIG. 1A, the Z-axis direction is assumed to be a rotation axis of a rotary frame 13 in a non-tilted state or a longitudinal direction of a tabletop 33 of the bed 30. Additionally, the X-axis direction is assumed to be an axial direction that is orthogonal to the Z-axis direction and horizontal with respect to a floor surface. The Y-axis direction is assumed to be an axial direction that is orthogonal to the Z-axis direction and perpendicular to the floor surface. FIG. 1A depicts the gantry 10 from a plurality of directions for explanation, and illustrates a case in which the X-ray CT apparatus 1 includes the one gantry 10.

The gantry 10 includes an X-ray tube 11, an X-ray detector 12, the rotary frame 13, an X-ray high voltage device 14, a control device 15, a wedge 16, a collimator 17, and a data acquisition system (DAS) 18.

The X-ray tube 11 is a vacuum tube including a cathode (filament) that generates thermoelectrons and an anode (target) that generates X-rays when the thermoelectrons collide therewith. The X-ray tube 11 generates X-rays to be applied to a subject P by applying thermoelectrons from the cathode toward the anode when a high voltage is applied from the X-ray high voltage device 14.

The X-ray detector 12 includes a plurality of detection elements (pixels), detects X-rays that have been emitted from the X-ray tube 11 and passed through the subject P, and outputs a detection signal corresponding to a detected X-ray dose to the DAS 18. Herein, the X-ray detector 12 is an example of a photon counting type (photon counting type) X-ray detector. For example, the X-ray detector 12 is a detector of direct conversion type that directly converts incident X-ray photons into electric signals. As a detector of direct detection type, for example, a semiconductor diode in which electrodes are attached to both ends of a semiconductor detector can be applied.

An X-ray photon incident on the semiconductor detector is converted into an electron-hole pair. The number of the electron-hole pairs generated by incidence of one X-ray photon depends on energy of the incident X-ray photon. The electron and the hole are respectively attracted to the pair of electrodes formed at both ends of the semiconductor detector, and the pair of electrodes generates an electric signal having a peak value corresponding to an electric charge of the electron-hole pair. One electric signal has a peak value corresponding to the energy of the incident X-ray photon.

The rotary frame 13 is a frame having an annular shape that supports the X-ray tube 11 and the X-ray detector 12 to be opposed to each other, and rotates the X-ray tube 11 and the X-ray detector 12 by the control device 15. For example, the rotary frame 13 is a casting made of aluminum as a material. The rotary frame 13 can further support the X-ray high voltage device 14, the wedge 16, the collimator 17, the DAS 18, and the like in addition to the X-ray tube 11 and the X-ray detector 12. In the following description, in the gantry 10, the rotary frame 13 and a portion that rotates and moves together with the rotary frame 13 are also referred to as rotation part (rotor). A portion that does not rotate in the gantry 10 is also referred to as fixed part (stator). The fixed part supports the rotation part.

The control device 15 performs operation control for the gantry 10 and the bed 30. The wedge 16 is an X-ray filter for adjusting a dose of X-rays emitted from the X-ray tube 11.

The collimator 17 is an X-ray diaphragm for narrowing down an irradiation range of X-rays transmitted through the wedge 16. A narrowing range of the collimator 17 can be mechanically driven.

The DAS 18 acquires signals of X-rays detected by the respective detection elements included in the X-ray detector 12. For example, the DAS 18 includes an amplifier that performs amplification processing on the electric signal output from each detection element and an A/D converter that converts the electric signal into a digital signal, and generates detection data.

The data generated by the DAS 18 is transmitted to a receiver including a photodiode disposed on a non-rotary portion (for example, a fixed frame and the like. Not illustrated in FIG. 1A) of the gantry 10 by optical communication from a transmitter including a light emitting diode (LED) disposed on the rotary frame 13, and transferred to the console 40. Herein, the non-rotary portion is, for example, a fixed frame or the like that supports the rotary frame 13 in a rotatable manner. A method for transmitting data from the rotary frame 13 to the non-rotary portion of the gantry 10 is not limited to the optical communication. Any data transmission scheme of non-contact type may be employed, or a data transmission scheme of contact type may be employed. The X-ray detector 12 and the DAS 18 may be formed as an integrated detector unit DU.

The bed 30 is an apparatus for placing and moving the subject P as a target of a CT scan, and includes a base 31, a bed drive device 32, the tabletop 33, and a support frame 34. The base 31 is a housing that supports the support frame 34 to be movable in a vertical direction. The bed drive device 32 is a driving mechanism that moves the tabletop 33 on which the subject P is placed in a long axis direction of the tabletop 33, and includes a motor, an actuator, and the like. The tabletop 33 disposed on an upper surface of the support frame 34 is a plate on which the subject P is placed. The bed drive device 32 may move the support frame 34 in the long axis direction of the tabletop 33 in addition to the tabletop 33.

The console 40 includes a memory 41, a display 42, an input interface 43, and processing circuitry 44. In the following description, the console 40 is separated from the gantry 10, but the gantry 10 may include the console 40 or some of constituent elements of the console 40.

The memory 41 is, for example, implemented by a semiconductor memory element such as a random access memory (RAM) and a flash memory, a hard disk, an optical disc, and the like. For example, the memory 41 stores projection data acquired by the CT scan, and an X-ray CT image reconstructed based on the projection data. The memory 41 also stores a computer program for circuit included in the X-ray CT apparatus 1 to implement a function thereof. The memory 41 may also be implemented by a server group (cloud) connected to the X-ray CT apparatus 1 via a network.

The display 42 displays various pieces of information under control by the processing circuitry 44. For example, the display 42 displays a graphical user interface (GUI) for receiving various instructions, settings, and the like from a user via the input interface 43. The display 42 also displays an image for display that is generated based on the X-ray CT image. For example, the display 42 is a liquid crystal display or a cathode ray tube (CRT) display. The display 42 may be a desktop type, or may be configured by a tablet terminal and the like that can wirelessly communicate with the processing circuitry 44.

The input interface 43 receives various input operations from the user, and converts the input operations into electric signals to be output to the processing circuitry 44. For example, the input interface 43 is implemented by a mouse or a keyboard, a trackball, a switch, a button, a joystick, a touch pad on which an input operation is performed by touching an operation surface, a touch screen obtained by integrating a display screen with a touch pad, a noncontact input circuit using an optical sensor, a voice input circuit, and the like. The input interface 43 may be configured by a tablet terminal and the like that can wirelessly communicate with the processing circuitry 44. The input interface 43 may be a circuit that receives an input operation from the user by motion capture. By way of example, the input interface 43 can receive body motion, a line of sight, and the like of the user as input operations by processing a signal acquired via a tracker or an image acquired for the user. The input interface 43 does not necessarily include a physical operation component such as a mouse or a keyboard. For example, examples of the input interface 43 include a processing circuit for an electric signal that receives an electric signal corresponding to an input operation from an external input appliance that is disposed separately from the X-ray CT apparatus 1, and outputs the electric signal to the processing circuitry 44.

The processing circuitry 44 controls the entire operation of the X-ray CT apparatus 1 by executing a control function 44*a* and an output function 44*b*. For example, the processing circuitry 44 functions as the control function 44*a* by reading out, from the memory 41, and executing a computer program corresponding to the control function 44*a*. Similarly, the processing circuitry 44 also functions as the output function 44*b*.

For example, the control function 44*a* controls operations of the gantry 10 and the bed 30 in accordance with an instruction from the user received via the input interface 43, and performs a CT scan on the subject P.

For example, the control function 44*a* supplies a high voltage to the X-ray tube 11 by controlling the X-ray high voltage device 14. Due to this, the X-ray tube 11 generates X-rays to be applied to the subject P. The control function 44*a* causes the subject P to move into a photographing port of the gantry 10 by controlling the bed drive device 32. The control function 44*a* also controls distribution of X-rays to be applied to the subject P by adjusting a position of the wedge 16, and an opening degree and a position of the collimator 17.

The control function 44*a* also detects the X-rays emitted from the X-ray tube 11 by controlling the X-ray detector 12 and the DAS 18, and acquires detection data. Specifically, as illustrated in FIG. 1B, the X-ray detector 12 includes a plurality of detection elements 12A and a voltage supply device 12B. The detection elements 12A are each constituted of a semiconductor detector and an electrode. In this configuration, when the X-rays are incident on the semiconductor detector, electric charges are generated inside the semiconductor detector. By applying a voltage to the semiconductor detector from the voltage supply device 12B via the electrode, the electric charges generated inside the semiconductor detector can be acquired.

That is, the detection element 12A is configured by combining the semiconductor detector with the electrode, and the detection elements 12A are configured by attaching a plurality of the electrodes to the semiconductor detector. The control function 44*a* then causes each of the detection elements 12A to output the electric charge by controlling an operation of the voltage supply device 12B and supplying a voltage to the detection elements 12A. The control function 44*a* also controls an operation of the DAS 18, and acquires detection data based on the electric charges output from the detection elements 12A.

The control function 44*a* can also perform various kinds of processing based on the detection data acquired by the CT scan. For example, the control function 44*a* performs preprocessing such as logarithm conversion processing, offset correction processing, sensitivity correction processing between channels, beam hardening correction, scattered ray correction, and dark count correction on the detection data output from the DAS 18. The detection data after being subjected to the preprocessing is also referred to as raw data. The detection data before being subjected to the preprocessing and the raw data after being subjected to the preprocessing are collectively referred to as projection data. Furthermore, the control function 44*a* generates an X-ray CT image by performing reconstruction processing on the projection data using a filtered back projection method, a successive approximation reconstruction method, and the like. Various kinds of data such as the projection data and the X-ray CT image are stored in the memory 41 as appropriate.

The output function 44*b* controls outputs of various kinds of data. For example, the output function 44*b* controls display on the display 42. For example, based on an input operation received from the user via the input interface 43, the output function 44*b* converts the X-ray CT image into an image for display such as an optional sectional image or a rendering image along an optional viewpoint direction to be displayed on the display 42. Additionally, for example, the output function 44*b* transmits various kinds of data such as the projection data and the X-ray CT image to an external image storage device to be stored therein.

In the X-ray CT apparatus 1 illustrated in FIG. 1A, processing functions are stored in the memory 41 in a form of a computer-executable computer program. The processing circuitry 44 is a processor that implements a function corresponding to each computer program by reading out, from the memory 41, and executing the computer program. In other words, the processing circuitry 44 that has read out the computer program has the function corresponding to the read-out computer program.

In FIG. 1A, it is assumed that the control function 44*a* and the output function 44*b* are implemented by the single processing circuitry 44. Alternatively, the processing circuitry 44 may be configured by combining a plurality of independent processors, and the functions may be implemented when the respective processors execute the computer programs. The processing functions of the processing circuitry 44 may be implemented by being appropriately distributed or integrated into a single processing circuit or a plurality of processing circuits.

The processing circuitry 44 may implement the function by using a processor of an external device connected thereto via a network NW. For example, the processing circuitry 44 implements the functions illustrated in FIG. 1A by reading out, from the memory 41, and executing the computer programs corresponding to the respective functions, and using, as a calculation resource, a server group (cloud) connected to the X-ray CT apparatus 1 via the network NW.

As illustrated in FIG. 1B, the X-ray detector 12 includes processing circuitry 12C. For example, the processing circuitry 12C functions as an identification function 12Ca by reading out, from a memory D, and executing a computer program corresponding to the identification function 12Ca. Similarly, the processing circuitry 12C also functions as a control function 12Cb.

The identification function 12Ca identifies target elements from among the detection elements 12A based on the information that is acquired during the CT scan using the X-ray detector 12, each of the target elements causing a large current to flow through a circuit between the target element and the voltage supply device 12B. The control function 12Cb stops voltage supply from the voltage supply device 12B to at least some of the target elements. The identification function 12Ca is an example of an identification unit. The control function 12Cb is an example of a control unit. Details about the processing performed by the identification function 12Ca and the control function 12Cb will be described later.

In the X-ray detector 12 illustrated in FIG. 1B, processing functions are stored in a memory 12D in a form of a computer-executable computer program. The processing circuitry 12C is a processor that implements a function corresponding to each computer program by reading out, from the memory 12D, and executing the computer program. In other words, the processing circuitry 12C that has read out the computer program has the function corresponding to the read-out computer program.

In FIG. 1B, it is assumed that the identification function 12Ca and the control function 12Cb are implemented by the single processing circuitry 12C. Alternatively, the processing circuitry 12C may be configured by combining a plurality of independent processors, and the functions may be implemented when the respective processors execute the computer programs. The processing functions of the processing circuitry 12C may be implemented by being appropriately distributed or integrated into a single processing circuit or a plurality of processing circuits.

In the above description, it is assumed that the single memory stores the computer programs corresponding to the respective processing functions of the processing circuit. However, the embodiment is not limited thereto. For example, a plurality of memories may be disposed in a distributed manner, and the processing circuit may be configured to read out a corresponding computer program from an individual memory. Instead of storing the computer program in the memory, the computer program may be directly incorporated in a circuit of the processor. In this case, the processor reads out and executes the computer program incorporated in the circuit to implement the function. For example, the processing circuitry 12C may be directly incorporated as a logic circuit in a circuit included in the X-ray detector 12. In this case, the X-ray detector 12 does not necessarily include the memory 12D.

The configuration example of the X-ray CT apparatus 1 has been described above. With this configuration, the X-ray CT apparatus 1 can avoid breakdown of the X-ray detector caused by a drop of a voltage used for acquiring electric charges in the CT scan using the photon counting type X-ray detector 12.

Figure 2:
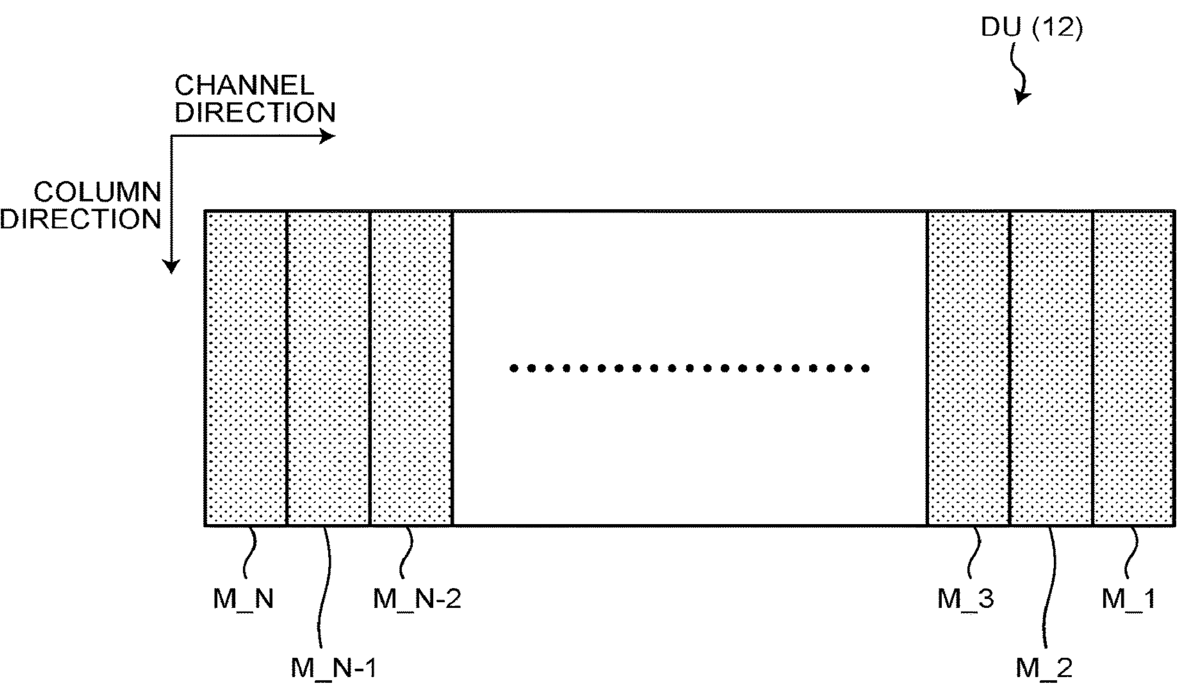
FIG. 2 is a diagram illustrating an example of the configuration of the X-ray detector according to the first embodiment.
Figure 3:
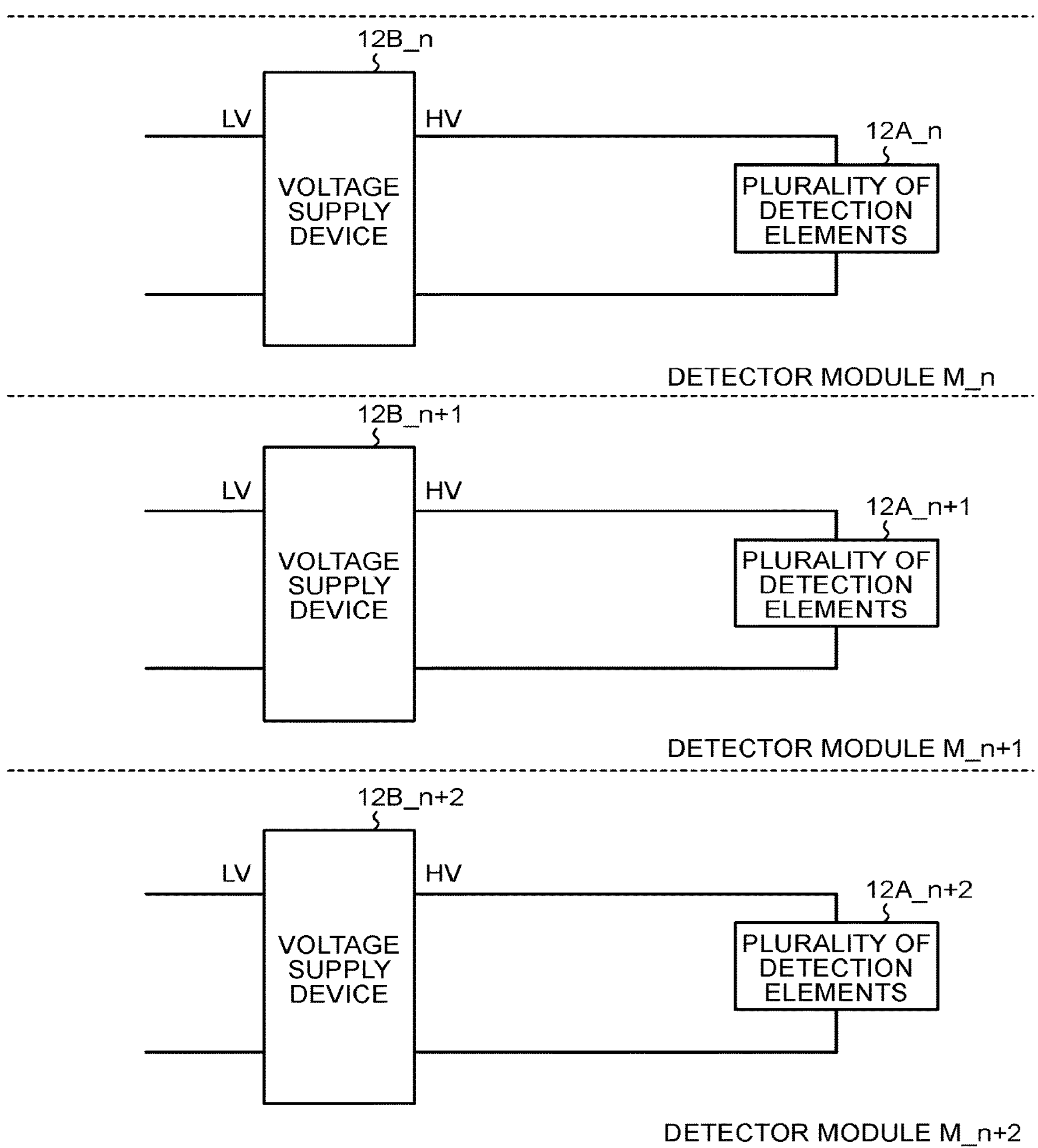
FIG. 3 is a diagram illustrating an example of the configuration of the X-ray detector according to the first embodiment.

First, with reference to FIG. 2 and FIG. 3, the following describes a specific configuration example of the X-ray detector 12. FIG. 2 and FIG. 3 are diagrams illustrating an example of the configuration of the X-ray detector 12 according to the first embodiment. The present embodiment describes an example in which the X-ray detector 12 and the DAS 18 are formed as the integrated detector unit DU.

FIG. 2 is a diagram illustrating the detector unit DU (X-ray detector 12) viewed from an X-ray incident direction. The detector unit DU illustrated in FIG. 2 is configured by arranging N detector modules M (detector modules M_1 to M_N) side by side in a channel direction.

The one detector module M includes a plurality of the detection elements A (detection element group). For example, as illustrated in FIG. 3, a detector module M_n, which is the n-th detector module M among the N detector modules M, includes a plurality of detection elements 12A_n. Similarly, a detector module M_n+1 includes a plurality of detection elements 12A_n+1. Similarly, a detector module M_n+2 includes a plurality of detection elements 12A_n+2.

FIG. 3 illustrates an example in which the one voltage supply device 12B is connected to each detection element group. For example, a voltage supply device 12B_n is connected to the detection elements 12A_n included in the detector module M_n. A voltage supply device 12B_n+1 is connected to the detection elements 12A_n+1 included in the detector module M_n+1. A voltage supply device 12B_n+2 is connected to the detection elements 12A_n+2 included in the detector module M_n+2.

The voltage supply device 12B applies a voltage (bias voltage) to the detection elements A. The voltage supply device 12B is, for example, a transformer (transformer) that boosts a low voltage (LV) supplied from a voltage power supply device (not illustrated) to a high voltage (HV), and supplies the boosted high voltage (HV) to the detection elements A.

A specific value of the voltage supplied from the voltage supply device 12B to the detection elements A is not particularly limited, but a high voltage may be applied in some cases depending on the configuration of the X-ray detector 12. For example, the semiconductor detector included in the X-ray detector 12 is implemented by CdTe or CdTeZn (CZT), a high voltage of about kV order is supplied to the detection elements A. For example, the semiconductor detector included in the X-ray detector 12 is implemented by Si, a high voltage of several kV equivalent to or higher than that for CdTe or CdTeZn is supplied to the detection elements A.

While the CT scan is performed, the control function 44*a* causes the voltage supply device 12B to supply a voltage to the detection elements 12A to cause the electric charges accumulated in the detection elements 12A to be output for each detector module M. Due to this, the control function 44*a* can acquire the electric charges accumulated in the detection elements 12A as detection signals.

Herein, the voltage used for acquiring the electric charges may drop in some cases corresponding to a dose of X-rays applied to the detection elements 12A. Specifically, in a case in which the dose of X-rays to be applied is large, a large number of electric charges may be generated in the detection elements 12A, and the voltage applied to the detection elements 12A may drop in some cases because a large current flows in the circuit at the time of acquiring the electric charges.

Such a voltage drop may be caused only in some of the detection elements 12A due to imbalance of the dose of X-rays. At this point, an artifact may be generated in a pixel corresponding to the detection element 12A in which a voltage drop is caused in the projection data acquired by the CT scan, and a fault of the X-ray detector 12 may be broken down in some cases. For example, in a case in which a voltage drop is caused in only some of the detector modules M, the X-ray detector 12 may be broken down in some cases because a potential difference is caused between itself and the adjacent detector module M and an electric discharge is caused. Specifically, an electric discharge is easily caused in a case in which an interval to the adjacent detector module M is short, and the X-ray detector 12 is often broken down in a case of using a high voltage for acquiring the electric charges.

As one means for avoiding breakdown of the X-ray detector 12, it can be considered that the voltage supply device 12B is designed to be compatible with a large current to prevent a voltage drop. For example, an upper limit value of a current that flows in the circuit is a value of a current that flows at the time when a maximum dose of X-rays that can be applied from the X-ray tube 11 is incident on the detection element 12A in a state of not being attenuated by the subject P and the like, and the upper limit value can be estimated. It can be considered that the voltage supply device 12B is designed to be compatible with the estimated upper limit value of the current. However, it is difficult to design the voltage supply device 12B to be compatible with a large current in view of implementation due to limitations on a size or cost.

Thus, the X-ray CT apparatus 1 according to the first embodiment avoids breakdown of the X-ray detector 12 in the CT scan using the photon counting type X-ray detector 12 through the processing performed by the processing circuitry 44 described below in detail. Specifically, the identification function 12Ca identifies the target elements from among the detection elements 12A based on the information that is acquired during the CT scan using the X-ray detector 12, each of the target elements causing a large current to flow through a circuit between the target element and the voltage supply device 12B. The control function 12Cb then stops voltage supply from the voltage supply device 12B to at least some of the target elements.

Figures 4, 5:
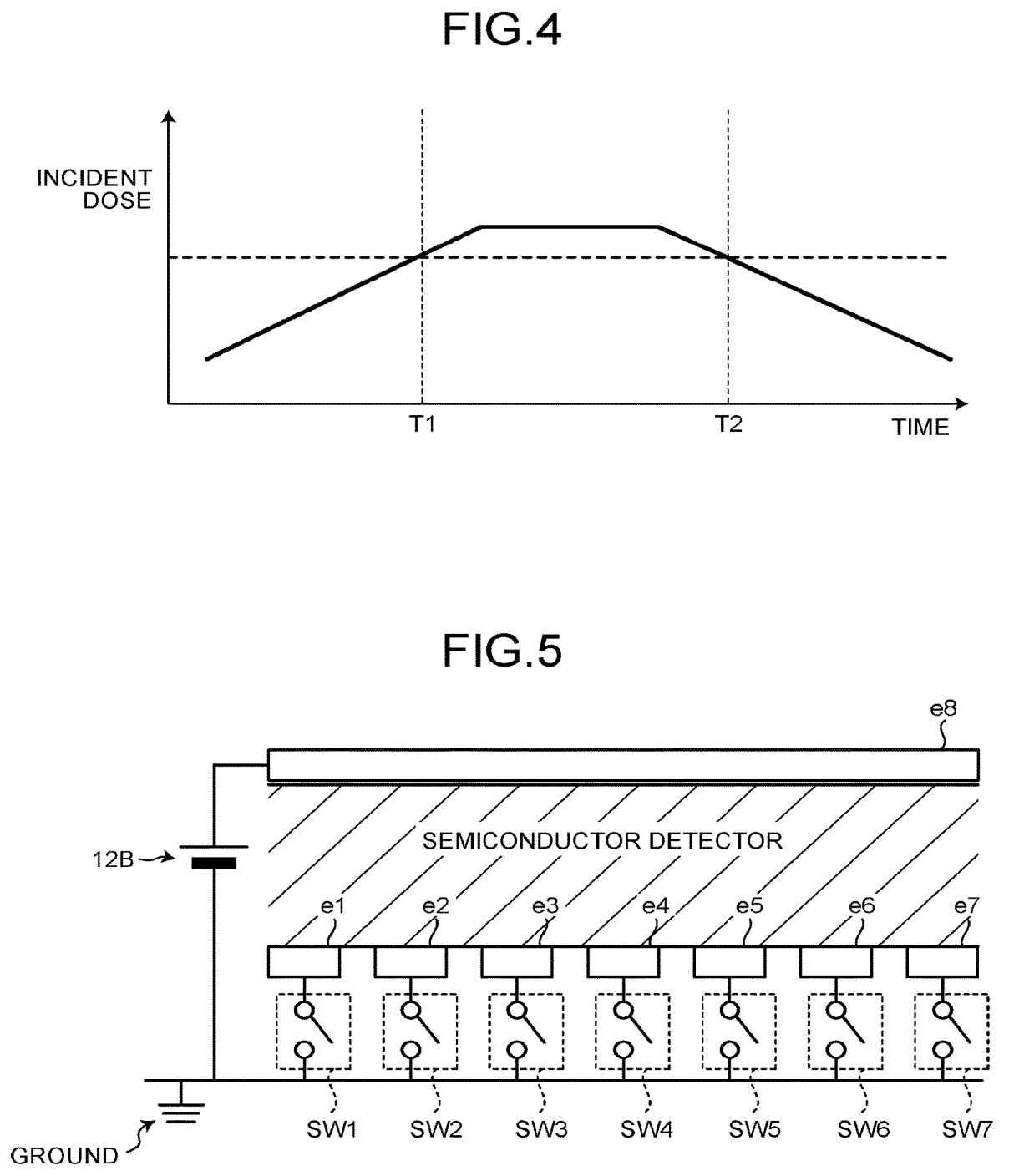

First, the following describes identification of the target elements by the identification function 12Ca with reference to FIG. 4. FIG. 4 illustrates an incident dose to a certain one of the detection elements 12A (hereinafter referred to as detection element 12Aa) as an example of the information that is acquired during the CT scan. Specifically, FIG. 4 illustrates a graph in which an elapsed time after the CT scan is started is associated with the incident dose to the detection element 12Aa.

The identification function 12Ca acquires the incident dose to the detection element 12Aa over time during the CT scan. The identification function 12Ca may generate the graph in FIG. 4, or simply acquire the incident dose over time without generating the graph. A horizontal axis in FIG. 4 may be replaced with the number of views.

For example, the identification function 12Ca acquires the incident dose to the detection element 12Aa based on a detection signal output from the detection element 12Aa. For example, the detection signal output from the detection element 12Aa becomes an electrical pulse having a larger peak value as the incident dose is larger. Thus, the identification function 12Ca can convert the peak value based on the detection signal into the incident dose. Additionally, in the projection data, a pixel value at a position corresponding to the detection element 12Aa becomes larger as the incident dose is larger. Thus, the identification function 12Ca can convert the pixel value based on the detection signal into the incident dose. The identification function 12Ca can receive a notification about the pixel value at the position corresponding to the detection element 12Aa from the DAS 18 or the console 40.

The identification function 12Ca may also acquire the incident dose to the detection element 12Aa based on detection signals output from the detection elements 12A (hereinafter referred to as peripheral elements) around the detection element 12Aa. For example, the identification function 12Ca acquires the incident dose to the detection element 12Aa based on an average value of the detection signals output from the peripheral elements. Alternatively, for each of the peripheral elements, the identification function 12Ca acquires the incident dose to the peripheral element based on the detection signal output from the peripheral element. The identification function 12Ca then acquires an average value of the incident dose to the peripheral elements as the incident dose to the detection element 12Aa.

In the example illustrated in FIG. 4, the incident dose to the detection element 12Aa is gradually increased after the CT scan is started. Such a chronological change of the incident dose may be caused by an increase in an output dose from the X-ray tube 11 in some cases, but may be caused even if the output dose is constant. For example, an irradiation angle of the X-ray is successively changed in the CT scan, so that the incident dose to the detection element 12Aa may be changed in some cases because a substance or a path length of the subject P present on the X-ray path to the detection element 12Aa is changed in some cases.

In the example illustrated in FIG. 4, the incident dose to the detection element 12Aa exceeds a threshold at time T1. Such a threshold is empirically set as an incident dose with which a drop of voltage applied to the detection element 12A is caused, for example. That is, in a case in which X-rays the dose of which is larger than the threshold are incident on the detection element 12Aa, a large current may flow through a circuit between the detection element 12Aa and the voltage supply device 12B, a voltage supplied from the voltage supply device 12B to the detection element 12Aa may drop, and breakdown of the X-ray detector 12 may be caused.

Thus, in a case in which the incident dose to the detection element 12Aa exceeds the threshold, the identification function 12Ca identifies the detection element 12Aa as the target element causing a large current to flow through a circuit between the target element and the voltage supply device 12B, and the control function 12Cb stops voltage supply to the target element from the voltage supply device 12B. Normally, the X-ray detector 12 includes a large number of minute detection elements 12A, so that the incident dose does not exceed the threshold in only one detection element 12A, but the incident dose exceeds the threshold in a plurality of the detection elements 12A substantially at the same time. In this case, the control function 12Cb stops voltage supply from the voltage supply device 12B to at least some of the target elements.

The following describes control of voltage supply to the target element with reference to FIG. 5. FIG. 5 is a schematic diagram of a circuit including the detection elements 12A and the voltage supply device 12B.

Specifically, the detection elements 12A are configured by electrodes e1 to e8 and a semiconductor detector illustrated in FIG. 5. For example, the first detection element 12A is configured by the electrode e1 on an anode side, the semiconductor detector, and the electrode e8 on a cathode side. That is, when an electric charge is generated in the semiconductor detector due to an incident X-ray and a voltage is applied from the voltage supply device 12B via the electrode e1 and the electrode e8, the generated electric charge is output from the electrode e1. The electric charge output from the electrode e1 is acquired by the DAS 18 as a detection signal obtained by the first detection element 12A.

Similarly, the second detection element 12A is configured by the electrode e2 on the anode side, the semiconductor detector, and the electrode e8 on the cathode side. The third detection element 12A is configured by the electrode e3 on the anode side, the semiconductor detector, and the electrode e8 on the cathode side. The fourth detection element 12A is configured by the electrode e4 on the anode side, the semiconductor detector, and the electrode e8 on the cathode side. The fifth detection element 12A is configured by the electrode e5 on the anode side, the semiconductor detector, and the electrode e8 on the cathode side. The sixth detection element 12A is configured by the electrode e6 on the anode side, the semiconductor detector, and the electrode e8 on the cathode side. The seventh detection element 12A is configured by the electrode e7 on the anode side, the semiconductor detector, and the electrode e8 on the cathode side.

Switches SW1 to SW7 illustrated in FIG. 5 are normally set to an ON state. Due to this, the DAS 18 can acquire the detection signals of the corresponding detection elements 12A via the electrodes e1 to e7 illustrated in FIG. 5.

Herein, for example, in a case in which the first detection element 12A including the electrode e1 is identified as the target element, the control function 12Cb turns off the switch SW1. Due to this, even if a large number of electric charges are generated due to the incident dose exceeding the threshold in the first detection element 12A including the electrode e1, the electric charges do not flow through the circuit. That is, a quantity of current flowing through the circuit in FIG. 5 can be suppressed, and a drop of the voltage applied from the voltage supply device 12B can be prevented.

For example, the first detection element 12A including the electrode e1 and the second detection element 12A including the electrode e2 are identified as the target elements, the control function 12Cb turns off the switch SW1 and the switch SW2. Alternatively, the control function 12Cb may turn off only one of the switch SW1 and the switch SW2. In many cases, the quantity of the current flowing through the circuit can be suppressed to the extent that a drop of the voltage applied from the voltage supply device 12B can be prevented by stopping only voltage supply to some of the target elements without stopping voltage supply to all of the target elements.

In performing control of stopping only voltage supply to some of the target elements, the control function 12Cb may set the detection element 12A (hereinafter also referred to as determined element) that stops voltage supply in a case of being identified as the target element.

Figure 6:
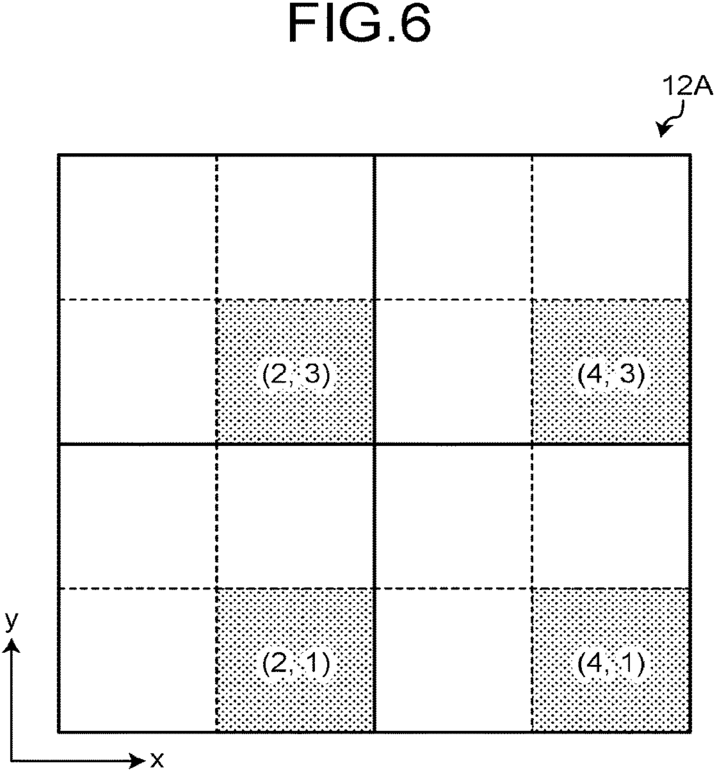
FIG. 6 is a diagram illustrating an example of a determined element according to the first embodiment.

FIG. 6 illustrates an example of the determined element. FIG. 6 illustrates 16 detection elements 12A arranged on a detection face. Coordinates are assigned to each of the detection elements 12A in FIG. 6. Specifically, the coordinates are assigned to each of the detection elements 12A such that the coordinates of the detection element 12A on the lower left are assumed to be (x, y)=(1, 1), the X-coordinate is incremented by "1" toward a right direction, and the Y-coordinate is incremented by "1" toward an upper direction.

In FIG. 6, a pattern is added to the determined element. Specifically, among the 16 detection elements 12A illustrated in FIG. 6, the detection element 12A at coordinates (2, 1), the detection element 12A at coordinates (4, 1), the detection element 12A at coordinates (2, 3), and the detection element 12A at coordinates (4, 3) are set as determined elements. That is, in FIG. 6, the determined element is set as every other one of the 16 detection elements 12A arranged on the detection face.

By setting the determined elements at regular intervals as illustrated in FIG. 6, it is possible to improve image quality obtained in a case of stopping voltage supply to the determined element. For example, in a case in which the detection element 12A at the coordinates (2, 3) is identified as the target element and voltage supply from the voltage supply device 12B is stopped, reading out of the electric charge from the detection element 12A at the coordinates (2, 3) is also stopped. Due to this, in the projection data of a view in which voltage supply to the detection element 12A at the coordinates (2, 3) is stopped, data missing is caused in a pixel corresponding to the detection element 12A at the coordinates (2, 3).

However, in a case illustrated in FIG. 6, the electric charges are continuously read out from the peripheral elements around the detection element 12A at the coordinates (2, 3), and data of the corresponding pixel is obtained. For example, the 8 detection elements 12A adjacent to the detection element 12A at the coordinates (2, 3) (the detection element 12A at coordinates (1, 2), the detection element 12A at coordinates (1, 3), the detection element 12A at coordinates (1, 4), the detection element 12A at coordinates (2, 2), the detection element 12A at coordinates (2, 4), the detection element 12A at coordinates (3, 2), the detection element 12A at coordinates (3, 3), and the detection element 12A at coordinates (3, 4)) are not the determined elements, so that the electric charges are continuously read out therefrom irrespective of the incident dose. In this way, in a case in which the data of the peripheral element is obtained, even if data missing is caused in the pixel corresponding to the detection element 12A at the coordinates (2, 3), it can be relatively easily corrected. For example, the control function 44*a* of the console 40 can complement the data of the pixel corresponding to the detection element 12A at the coordinates (2, 3) by linear complement based on data of the peripheral elements.

FIG. 5 exemplifies a case of disposing the switches for all of the detection elements 12A in the drawing, but the switches may be disposed for only some of the detection elements 12A. For example, the switches may be disposed for only the determined elements.

Returning to FIG. 4, the description will be continued. In the example illustrated in FIG. 4, the incident dose to the detection element 12Aa exceeds the threshold at the time T1, and after the voltage supply to the detection element 12Aa is stopped, the incident dose falls below the threshold at time T2. At this point, the control function 12Cb may resume the voltage supply to the detection element 12Aa. The detection signal is not output from the detection element 12Aa during a period in which the voltage supply to the detection element 12Aa is stopped, so that the incident dose to the detection element 12Aa cannot be acquired based on the detection signal output from the detection element 12Aa. However, even in such a situation, the identification function 12Ca can acquire the incident dose to the detection element 12Aa based on the detection signal output from the peripheral element around the detection element 12Aa.

Alternatively, when the incident dose falls below the threshold at the time T2 in FIG. 4, the control function 12Cb does not necessarily resume the voltage supply to the detection element 12Aa. Typically, the electric charges generated in the semiconductor detector remain in the semiconductor detector until being discharged from the semiconductor detector by an applied voltage. Thus, in a case of stopping reading out of the electric charges from the detection element 12Aa and resuming reading out of the electric charges later, remaining electric charges are output as detection signals for a while after the resumption, so that artifacts are generated and correction processing is required. Due to outputs of the remaining electric charges, a large current may flow through the circuit and cause a voltage drop. According to the above description, the control function 12Cb does not necessarily resume the voltage supply to the detection element 12A for which voltage supply has been once stopped, until the CT scan is ended.

As described above, the X-ray detector 12 according to the embodiment is a photon counting type X-ray detector, and includes the detection elements 12A, the voltage supply device 12B, the identification function 12Ca, and the control function 12Cb. The voltage supply device 12B supplies the detection elements A with a voltage for reading out the electric charges accumulated in the detection elements A irradiated with X-rays. The identification function 12Ca identifies target elements from among the detection elements 12A based on the information that is acquired during the CT scan using the X-ray detector 12, each of the target elements causing a large current to flow through a circuit between the target element and the voltage supply device 12B. The control function 12Cb stops voltage supply to at least some of the target elements. Due to this, the X-ray detector 12 according to the embodiment can avoid breakdown caused by a drop of the voltage used for acquiring the electric charges in the CT scan using the photon counting type X-ray detector.

As described above, when the target elements are identified by the identification function 12Ca, the control function 12Cb stops voltage supply from the voltage supply device 12B to the determined elements among the target elements. Due to this, the control function 12Cb can improve image quality of a reconstructed X-ray CT image. That is, in a case of stopping voltage supply to some of the detection elements 12A, data missing is caused in each of pixels corresponding to these detection elements 12A in the projection data. However, by setting the detection element 12A for which voltage supply is stopped is set as the "determined element" in advance, data missing in the peripheral elements can be prevented, for example, and complement processing can be easily performed with high accuracy. By extension, a high-quality X-ray CT image can be reconstructed based on the projection data subjected to appropriate complement processing.

In the first embodiment described above, the incident dose to the detection element 12Aa is exemplified as information that is acquired during the CT scan. On the other hand, the second embodiment describes a measured value of a voltage supplied from the voltage supply device 12B to the detection element 12A as an example of the information that is acquired during the CT scan. That is, the second embodiment describes a case of identifying the target element based on the measured value of the voltage. Hereinafter, the same point as that in the description of the first embodiment is denoted by the same reference numeral, and the description thereof will not be repeated.

Figure 7:
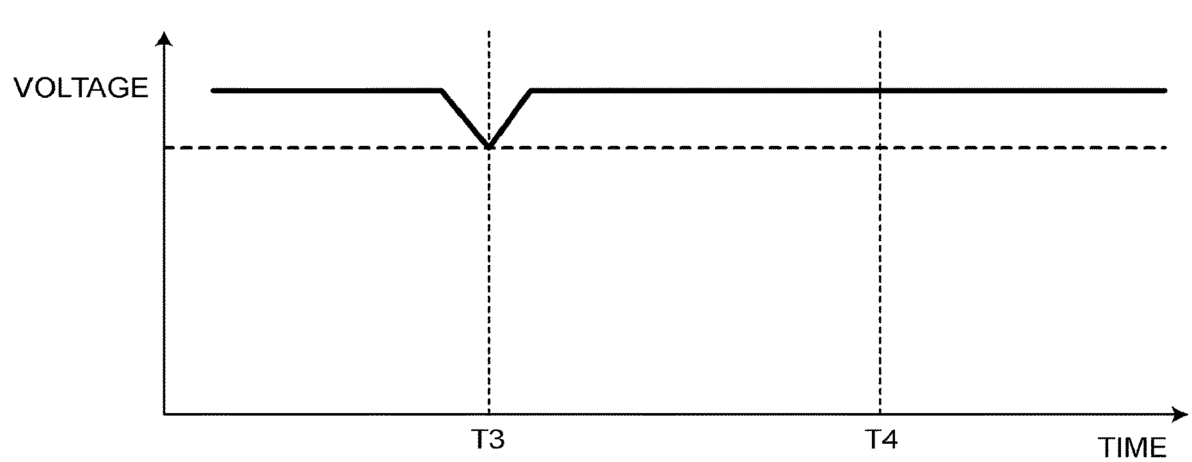
FIG. 7 is a diagram illustrating an example of information that is acquired during a CT scan according to a second embodiment.
Figure 8:
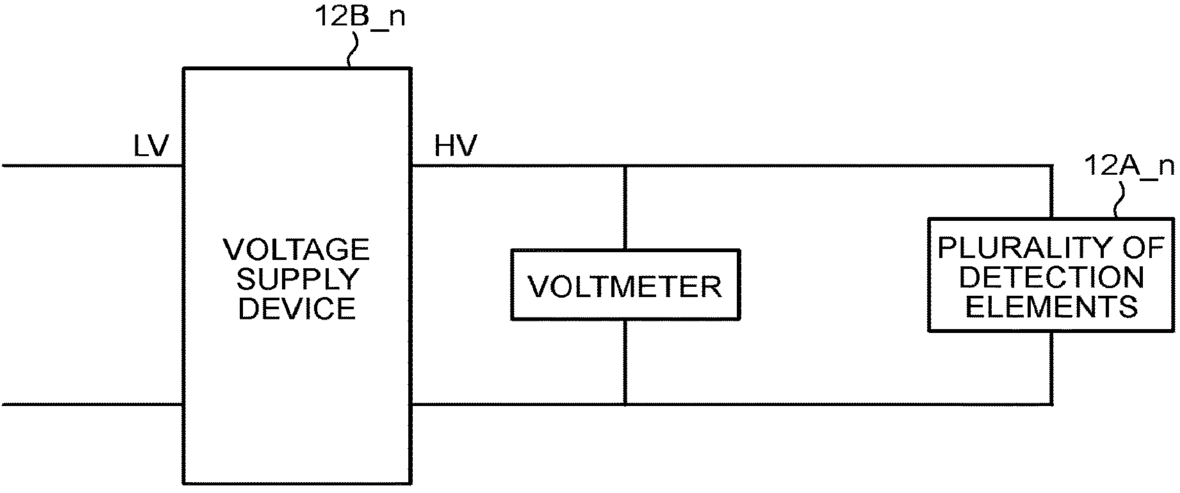
FIG. 8 is a diagram illustrating an example of a voltmeter according to the second embodiment.

The following describes identification of the target element based on the measured value of the voltage with reference to FIG. 7 and FIG. 8. FIG. 7 illustrates a graph in which the elapsed time after the CT scan is started is associated with the measured value of the voltage. The identification function 12Ca measures the voltage over time during the CT scan. Similarly to the case of FIG. 4, the identification function 12Ca may generate the graph in FIG. 7, or simply measure the voltage over time without generating the graph. A horizontal axis in FIG. 7 may be replaced with the number of views.

The voltage illustrated in FIG. 7 is, for example, measured by a voltmeter illustrated in FIG. 8. Similarly to FIG. 3, FIG. 8 illustrates the voltage supply device 12B_n as an example of the voltage supply device 12B. The voltage supply device 12B_n supplies the detection elements 12A_n with a voltage for reading out the electric charges accumulated in the detection elements.

In the example illustrated in FIG. 7, a voltage drop is caused at time T3, and the voltage falls below the threshold indicated by a dotted line in the drawing. That is, at the time T3, a large dose of X-rays is incident on the detection elements 12A_n, a large current flows through the circuit between the detection elements 12A_n and the voltage supply device 12B_n, and the voltage supplied from the voltage supply device 12B_n to the detection elements 12A_n drops. At this point, the identification function 12Ca identifies the detection elements 12A_n as the target elements.

At this point, the control function 12Cb stops voltage supply to at least some of the detection elements 12A_n identified as the target elements. That is, as described above in the first embodiment, breakdown of the X-ray detector 12 can be avoided by stopping voltage supply to all of the detection elements 12A_n. For example, by stopping voltage supply to some of the detection elements 12A_n such that only the voltage supply to the determined elements is stopped, image quality of a reconstructed X-ray CT image can be improved while avoiding breakdown of the X-ray detector 12 and allowing the complement processing for missing data to be easily performed with high accuracy.

In FIG. 7, a voltage drop is caused at the time T3, and voltage supply to at least some of the detection elements 12A_n identified as the target elements is stopped, so that the current flowing through the circuit is reduced, and the voltage is maintained after the time T3. Herein, after the time T3, the current flowing through the circuit is increased again at the time of resuming the voltage supply to the detection element 12A for which voltage supply has been stopped. However, it is unclear whether a voltage drop is caused thereby similarly to that at the time T3 from the information in FIG. 7. Thus, the control function 12Cb does not necessarily resume the voltage supply to the detection element 12A for which voltage supply has been once stopped, until the CT scan is ended.

In the embodiment described above, exemplified is a case in which the X-ray detector 12 and the DAS 18 are formed as the integrated detector unit DU. However, the embodiment is not limited thereto, and can be similarly applied to the X-ray detector 12 as a single item.

In the embodiment described above, exemplified is a case of identifying the target elements from among the detection elements 12A based on the information that is acquired during the CT scan, each of the target elements causing a large current to flow through the circuit between the target element and the voltage supply device 12B. However, the embodiment is not limited thereto, and the target element may be identified based on information acquired in advance. For example, in the CT scan, a positioning scan is previously performed in some cases. Specifically, after the subject P is placed on the tabletop 33, the positioning scan is performed first, a photographing range is set based on a positioning image acquired by the positioning scan, and the CT scan (main scan) for c acquiring an image for diagnosis is performed for the set photographing range. The positioning image is also called a scanogram (scano-image), a scout image, or the like. The identification function 12Ca can identify the target element causing a large current to flow through a circuit between the target element and the voltage supply device 12B based on the positioning image acquired by the positioning scan.

Specifically, the identification function 12Ca can estimate the detection element 12A on which a large dose of X-rays is incident for each irradiation angle (view) of the X-ray based on the positioning image. For example, based on the positioning image, the identification function 12Ca can estimate a range in which the subject P is present in a photographing space, and estimate the detection element 12A on which the X-ray is incident without being transmitted through the subject P. The identification function 12Ca can also estimate the detection element 12A on which the X-ray is incident, the X-ray that has been transmitted through the subject P but is not almost attenuated due to a path length of the subject P present on an X-ray path, a substance, and the like. A large current flows through the circuit between the detection element 12A on which a large dose of X-rays is incident and the voltage supply device 12B, so that the identification function 12Ca can identify, as the target element, the detection element 12A on which a large dose of X-rays is incident.

The processing performed by the identification function 12Ca and the control function 12Cb described above may be performed by the processing circuitry 44 of the console 40. That is, functions corresponding to the identification function 12Ca and the control function 12Cb described above may be implemented by the processing circuitry 44. For example, the processing circuitry 44 identifies the target elements from among the detection elements 12A based on the information that is acquired during the CT scan, each of the target elements causing a large current to flow through the circuit between the target element and the voltage supply device 12B, and stops voltage supply from the voltage supply device 12B to at least some of the target elements.

The word of "processor" used in the above description means, for example, a circuit such as a CPU, a Graphics Processing Unit (GPU), an ASIC, and a programmable logic device (for example, a simple programmable logic device (SPLD), a complex programmable logic device (CPLD), and a field programmable gate array (FPGA)). In a case in which the processor is a CPU, for example, the processor implements a function by reading out and executing a computer program stored in a storage circuit. On the other hand, in a case in which the processor is an ASIC, for example, the function is directly incorporated as a logic circuit in the circuit of the processor instead of storing the computer program in the storage unit. Each of processors in the embodiment is not necessarily configured as a single circuit. A plurality of independent circuits may be combined to be one processor to implement the function thereof. Furthermore, a plurality of constituent elements in the respective drawings may be integrated into one processor to implement the function thereof.

The constituent elements of the devices according to the embodiment described above are merely conceptual, and it is not required that they are physically configured as illustrated necessarily. That is, specific forms of distribution and integration of the devices are not limited to those illustrated in the drawings. All or part thereof may be functionally or physically distributed/integrated in arbitrary units depending on various loads or usage states. Furthermore, all or optional part of the processing functions performed by the respective devices may be implemented by a CPU and a computer program analyzed and executed by the CPU, or may be implemented as hardware using wired logic.

The control method for the photon counting type X-ray detector described above in the embodiment can be implemented by executing a computer program prepared in advance by a computer such as a personal computer or a workstation. This computer program can be distributed via a network such as the Internet. This computer program may be recorded in a computer-readable non-transitory recording medium such as a hard disk, a flexible disk (FD), a CD-ROM, an MO, or a DVD, and executed by being read out from the recording medium by the computer.

According to at least one of the embodiments described above, it is possible to avoid breakdown of the X-ray detector caused by a drop of the voltage used for acquiring the electric charges in the CT scan using the photon counting type X-ray detector.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray detector of photon counting type comprising a plurality of detection elements and a voltage supply device configured to supply the detection elements with a voltage for reading out electric charges accumulated in the detection elements irradiated with X-rays, the X-ray detector comprising:

processing circuitry configured to identify target elements from among the detection elements of the X-ray detector based on information that is acquired during a CT scan using the X-ray detector, each of the target elements causing a large current to flow through a circuit between the target element and the voltage supply device, and stop voltage supply from the voltage supply device to at least some of the target elements.

2. The X-ray detector according to claim 1, wherein the processing circuitry stops voltage supply from the voltage supply device to determined elements among the target elements.

3. The X-ray detector according to claim 2, wherein the determined elements are set at regular intervals with respect to the detection elements arranged on a detection face.

4. The X-ray detector according to claim 1, wherein the processing circuitry identifies the target element based on an incident dose to the detection element.

5. The X-ray detector according to claim 1, wherein the processing circuitry identifies the target element based on a measured value of a voltage supplied from the voltage supply device to the detection element.

6. A control method for an X-ray detector of photon counting type comprising a plurality of detection elements and a voltage supply device configured to supply the detection elements with a voltage for reading out electric charges accumulated in the detection elements irradiated with X-rays, the control method comprising:

identifying target elements from among the detection elements of the X-ray detector based on information that is acquired during a CT scan using the X-ray detector, each of the target elements causing a large current to flow through a circuit between the target element and the voltage supply device, and stopping voltage supply from the voltage supply device to at least some of the target elements.

* * * * *